US008467971B2

(12) United States Patent
Zemla et al.

(10) Patent No.: US 8,467,971 B2
(45) Date of Patent: Jun. 18, 2013

(54) STRUCTURE BASED ALIGNMENT AND CLUSTERING OF PROTEINS (STRALCP)

(75) Inventors: Adam T. Zemla, Brentwood, CA (US); Carol E. Zhou, Pleasanton, CA (US); Jason R. Smith, Mountain House, CA (US); Marisa W. Lam, Pleasanton, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 892 days.

(21) Appl. No.: 11/890,863

(22) Filed: Aug. 7, 2007

(65) Prior Publication Data

US 2008/0033659 A1    Feb. 7, 2008

Related U.S. Application Data

(60) Provisional application No. 60/836,434, filed on Aug. 7, 2006.

(51) Int. Cl.
*G01N 33/48* (2006.01)
*G06F 19/00* (2006.01)

(52) U.S. Cl.
USPC .............................................. 702/19; 703/11

(58) Field of Classification Search
None
See application file for complete search history.

(56) References Cited

U.S. PATENT DOCUMENTS

| 7,231,301 B2 | 6/2007 | Doi et al. |
| 2002/0150906 A1 | 10/2002 | Debe |
| 2003/0130797 A1 | 7/2003 | Skolnick et al. |
| 2004/0185486 A1 | 9/2004 | Zemla |
| 2005/0089878 A1 | 4/2005 | Debe et al. |

FOREIGN PATENT DOCUMENTS

| WO | WO 93/01484 | 1/1993 |
| WO | WO 98/48270 | 10/1998 |
| WO | WO 00/11206 | 3/2000 |
| WO | WO 03/048724 | 6/2003 |

OTHER PUBLICATIONS

Cristobal et al. BMC Bioinformatics 2001, 2:5. Published Aug. 1, 2001.*
Zemla et al. Proteins: Structure, Function, and Genetics vol. 45, Issue S5, pp. 13-21. Published Online: Jan. 28, 2002.*
Zemla et al. Nucleic Acids Research, 2003, vol. 31, No. 13, p. 3370-3374.*
Al-Lazikani, B. et al., "Combining Multiple Structure and Sequence Alignments to Improve Sequence Detection and Alignment: Application to the SH2 Domains of Janus Kinases," *PNAS*, Dec. 18, 2001, pp. 14796-14801, vol. 98, No. 2.
Altschul, S.F. et al., "Gapped BLAST and PSI-BLAST: A New Generation of Protein Database Search Programs," *Nucleic Acids Research*, 1997, pp. 3389-3402, vol. 25.
Aung, Z. et al., "Automatic 3D Protein Structure Classification without Structural Alignment," *Journal of Computational Biology*, 2005, pp. 1221-1241, vol. 12, No. 9.
Bonneau, R. et al., "Functional Inferences from Blind ab Initio Protein Structure Predictions," *Journal of Structural Biology*, 2001, pp. 186-190, vol. 134.
Brady, G.P. et al., "Fast Prediction and Visualization of Protein Binding Pockets with PASS," *Journal of Computer-Aided Molecular Design*, 2000, pp. 383-401, vol. 14.
Canutescu, A. et al., A Graph-theory Algorithm for Rapid Protein Side-chain Prediction, *Protein Science*, 2003, pp. 2001-2014, vol. 12.
Cheek, S. et al., "SCOPmap: Automated assignment of protein structures to evolutionary superfamilies," *BMC Bioinformatics*, 2004, p. 197, vol. 5.
Chen, B.Y. et al., "Algorithms for structural comparison and statistical analysis of 3D protein motifs," *Pacific Symposium on Biocomputing*, 2005, pp. 334-345, vol. 10.
Dantas, G., "A Large Scale Test of Computational Protein Design: Folding and Stability of Nine Completely Redesigned Globular Proteins," *Journal of Molecular Biology*, 2003, pp. 449-460, vol. 332.
Fofanov, C. et al., "Fast Algorithm for the Analysis of the Presence of Short Oligonucleotide Subsequences in Genomic Sequences," *Technical Report No. UH-CS-05-11*, Department of Computer Science, University of Houston, USA, May 3, 2005, eight pages.
Fukunishi, Y. et al., "Similarities among Receptor Pockets and among Compounds: Analysis and Application to in silico Ligand Screening," *Journal of Molecular Graphics and Modelling*, 2005, pp. 34-45, vol. 24.
Gront, D. et al., "HCPM—Program for Hierarchical Clustering of Protein Models," *Bioinformatics*. Jul. 15; 2005, pp. 3179-3180, vol. 21, No. 14, Epub Apr 19, 2005.
Heller, K.A. et al., "Bayesian Hierarchical Clustering," ACM International Conference Proceeding Series, 2005, pp. 297-304, vol. 119, ISBN: 1-59593-180-5. ACM Press.
Holm, L. et al., "Protein Structure Comparison by Alignment of Distance Matrices," *Journal of Molecular Biology*, 1993, pp. 123-138, vol. 233.
Huan, J. et al., "Accurate Classification of Protein Structural Families Using Coherent Subgraph Analysis," *Pac. Symp. Biocomput*, 2004, pp. 411-422.
Lackner, P. et al., "ProSup: A Refined Tool for Protein Structure Alignment," *Protein Engineering*, 2000, vol. 13, pp. 745-752, No. 11.
Moult, J. et al., "Critical Assessment of Methods of Protein Structure Prediction (CASP)-Round V", Proteins: Structure, Function, and Genetics, 2003, pp. 334-339, vol. 53, Issue S6.

(Continued)

*Primary Examiner* — Michael Borin
(74) *Attorney, Agent, or Firm* — Fenwick & West, LLP

(57) ABSTRACT

Disclosed are computational methods of clustering a set of protein structures based on local and pair-wise global similarity values. Pair-wise local and global similarity values are generated based on pair-wise structural alignments for each protein in the set of protein structures. Initially, the protein structures are clustered based on pair-wise local similarity values. The protein structures are then clustered based on pair-wise global similarity values. For each given cluster both a representative structure and spans of conserved residues are identified. The representative protein structure is used to assign newly-solved protein structures to a group. The spans are used to characterize conservation and assign a "structural footprint" to the cluster.

21 Claims, 10 Drawing Sheets
(3 of 10 Drawing Sheet(s) Filed in Color)

OTHER PUBLICATIONS

Orengo, C.A. et al., "CATH—A Hierarchic Classification of Protein Domain Structures," *Structure*, 1997, pp. 1093-1108, vol. 5, No. 8.

Ortiz, A.R., "MAMMOTH (Matching Molecular Models Obtained from Theory): An Automated Method for Model Comparison," *Protein Science*, 2002, pp. 2606-2621, vol. 11.

Shindyalov, I. et al., "Protein Structure Alignment by Incremental Combinatorial Extension (CE) of the Optimal Path," *Protein Engineering*, 1998, pp. 739-747, vol. 11, No. 9.

United States Office Action, U.S. Appl. No. 10/782,061, Jan. 4, 2007, thirteen pages.

United States Office Action, U.S. Appl. No. 10/782,061, Sep. 24, 2007, fourteen pages.

United States Office Action, U.S. Appl. No. 10/782,061, Jun. 11, 2008, fifteen pages.

United States Office Action, U.S. Appl. No. 10/782,061, Jun. 23, 2009, fifteen pages.

United States Office Action, U.S. Appl. No. 11/735,972, Dec. 23, 2010, eight pages.

United States Office Action, U.S. Appl. No. 11/735,981, Apr. 28, 2010, thirteen pages.

United States Office Action, U.S. Appl. No. 11/735,981, Jan. 6, 2011, twelve pages.

United States Office Action, U.S. Appl. No. 11/818,075, May 11, 2009, sixteen pages.

United States Office Action, U.S. Appl. No. 11/818,075, May 26, 2010, twenty pages.

United States Office Action, U.S. Appl. No. 11/818,075, Jan. 3, 2011.

United States Office Action, U.S. Appl. No. 11/890,864, Apr. 28, 2010, fifteen pages.

United States Office Action, U.S. Appl. No. 11/890,864, Dec. 21, 2010, twelve pages.

U.S. Appl. No. 60/451,292, Feb. 18, 2004. Local-global alignment for finding 3D similarities in protein structures.

Zemla, A. et al., "AS2TS System for Protein Structure Modeling and Analysis," *Nucleic Acids Research*, 2005, pp. W111-W115, vol. 33, Web Server Issue.

Zemla, A. et al., "Processing and Analysis of CASP3 Protein Structure Predictions," *Proteins: Structure, Function, and Genetics*, 1999, pp. 22-29, vol. 27, Issue Suppl. 3.

Zhang, C. et al., "Overview of Structural Genomics: From Structure to Function," *Current Opinion in Chemical Biology*, 2003, pp. 28-32, vol. 7.

Zhou, C. et al., "Computational Approaches for Identification of Conserved/Unique Binding Pockets in the A Chain of Ricin," *Bioinformatics*, May 19, 2005, pp. 3089-3096, vol. 21, No. 14.

Zhou, C. et al., "MannDB—A Microbial Database of Automated Protein Sequence Analyses and Evidence Integration for Protein Characterization," *BMC Bioinformatics*, Oct. 17, 2006, six pages.

Zhou, C. et al., "MvirDB—A Microbial Database of Protein Toxins, Virulence Factors and Antibiotic Resistance Genes for Bio-defence Applications," *Nucleic Acids Research*, 2006, pp. D1-D4, vol. 00, Database Issue.

Zu-Kang, F. et al., "Optimum Superimposition of Protein Structures: Ambiguities and Implications," Research Paper, *Folding & Design*, Feb. 26, 1996, vol. 1, pp. 123-132, No. 2, Salzburg, Austria.

\* cited by examiner

| Cluster   | Name    |         |         |         |         |         |         |         |
|-----------|---------|---------|---------|---------|---------|---------|---------|---------|
| Cluster:1 | d1f77a2 | .#..#.#####....##..###############...######....######............#### | | | | | | |
| Cluster:1 | d1ck1a2 | .G..V.VDGIQ...RT.KKNVTLQELDIKIRKILSDKYKI...KGLIEPDM....YSFDI...YEIDKIYEDNKTLKS....DVNL. | | | | | | |
| Cluster:1 | d1goza2 | .L..V.ENKRN...QT.KKSVTAQELDIKARNFLINKKNL..TGYIKPIE....FMYDM...SKYLMIYKDNKMVDS...EVHL. | | | | | | |
| Cluster:1 | d1bxta2 | .T..V.EDGKN...QT.KKGKVTAQELDYLTRHYLVKNKGL..TGYIKPIE....FMYDM...SKYLMYNDNKMVDS...EVYL. | | | | | | |
| Cluster:1 | d1uupa2 | .T..V.EDNEN...TT.KKQVTVQELDCKTRKILVSRKNL..TGYIKPIE....FMYDM...SKYLALYNDNKTVSS...EVHL. | | | | | | |
| Cluster:1 | d1fnua2 | .V..V.IDGIQ...ET.KKAVTAQELDYKVRKYLTDNKQL..TGYIKPIP....FMFDP...SKYLMIYKDNETLDS...EVYL. | | | | | | |
| Cluster:1 | d1esfa2 | .V..V.IDGIQ...ET.KKAVTAQELDYKVRKYTIDNKQL..TGYIKPIP....FMFDF...SKYLMIYKDNETLDN...EVYL. | | | | | | |
| Cluster:1 | d1ewca2 | .P..L.LDGKQ...KT.KKNVTVQELDLDLQARRYLQEKYNL..RGLIVFHT...VNYDL...NTLLRIYRDNKTINS...DIYL. | | | | | | |
| Cluster:1 | d1ty0a2 | .G..V.VDGIQ...RT.KKNVTLQELDIKIRKILSDKYKI...KGLIEPDM....YSFDI...YEIDKIYEDNKTLKS....DVNL. | | | | | | |
| Cluster:1 | d1et9a2 | .V..L.IDGVQ...KI.KPIFTIQEFDFKIRQYLMQYYKI...KGQLEIAI....ESFNL...SDIFKKYKDNKTINM....DIYL. | | | | | | |
| Cluster:1 | d1lo5d2 | .P..V.DKSKQ...TV.KPKVTAQEVDIKVRKLLIKKYDI..KGTVTLDL....IVFDL...NSMLKIYSNNERIDS...DVSI. | | | | | | |
| Cluster:1 | d1sebd2 | .P..L.LDGKQ...KT.KKNVTVQELDLDLQARRYLQEKYNL..RGLIVFHT...VNYDL...NTLLRIYRDNKTINS...AIYL. | | | | | | |
| Cluster:1 | d1hqrd2 | .T..V.EDGKN...QT.KKKKVTAQELDYLTRHYLVRNKKL..TGYIKPIE....FMYDM...SKYLMAYNDNKMVDS...EVYL. | | | | | | |
|           |         | .L..L.ISGES...IL.KDIVTFQEIDFKIRKYLMDNYKI..SGRIEIGT....EQIDL...SDIFAKYKDNRIINM....DIYL. | | | | | | |
| Cluster   | Name    | ....####.......####.........###############...###########........######### | | | | | | |
| Cluster:2 | d1m4va2 | ...VIKK......YIYKE......KELDFKLRQYLIQ.......KIKVIMKDGGYYTFELN.......DGRNIEKMEAN. | | | | | | |
| Cluster:2 | d2tssa2 | ...KVKV......KFDKK......STLDFEIRHQLTQ.......YMKITMNDGSTYQSDLS.......NIDEIKTIEAE. | | | | | | |
| Cluster:2 | d1aw7a2 | ...KVKV......KFDKK......STLDFEIRHALTQ.......YMKITMNDGSTYQSDLS.......NIDEIKTIEAE. | | | | | | |
| Cluster:2 | d1v1pa2 | ...FVNK......LIQKE......KELDFKIRQQQLVN......KIINLKDENKVEIDLG.......NSKDIRGISVT. | | | | | | |
| Cluster:2 | lyn3_A  | ...TITV......TPNKN......KDLEGKVKSVLES.......KTVNFKNGTKKVIDLK.......NSSDIKSININ. | | | | | | |
| Cluster:2 | lyn4_A  | ...TISV......VFPEN......QEIDSKVKNELAS.......TYTLILNDGNKKVVNLK.......DPSTKQIQIV. | | | | | | |
| Cluster:2 | lyn5_A  | ...TIAV......NLPKD......LDLGNKVKALLYD.......VTVTMKDGSKKEVDLK.......DSNSIKQIDIN. | | | | | | |

FIG. 7

| SCOP Fold | Nd | Ns | Nf | Nc | MC |
|---|---|---|---|---|---|
| Fold a.5 | 70 | 9 | 13 | 22 | 6.82 |
| Fold a.7 | 95 | 11 | 12 | 23 | 2.17 |
| Fold a.8 | 57 | 7 | 10 | 11 | 4.55 |
| Fold a.24 | 352 | 23 | 29 | 43 | 2.33 |
| Fold a.29 | 63 | 6 | 7 | 9 | 5.56 |
| Fold b.2 | 292 | 10 | 23 | 41 | 0.00 |
| Fold b.42 | 276 | 8 | 12 | 20 | 10.00 |
| Fold b.43 | 201 | 4 | 7 | 14 | 0.00 |
| Fold b.80 | 122 | 7 | 17 | 20 | 0.00 |
| Fold b.85 | 176 | 7 | 9 | 12 | 0.00 |
| Fold c.8 | 296 | 8 | 10 | 11 | 0.00 |
| Fold c.51 | 112 | 4 | 7 | 7 | 0.00 |
| Fold d.52 | 51 | 7 | 7 | 15 | 0.00 |
| Fold d.68 | 93 | 7 | 9 | 16 | 3.12 |
| Fold d.79 | 212 | 7 | 10 | 16 | 0.00 |
| Fold d.110 | 151 | 7 | 17 | 20 | 2.50 |
| Fold d.129 | 209 | 8 | 13 | 18 | 0.00 |
| Fold f.4 | 116 | 6 | 11 | 23 | 0.00 |
| Fold g.41 | 297 | 13 | 21 | 32 | 1.56 |
| Fold h.4 | 55 | 16 | 16 | 20 | 2.50 |
| Total in Folds | 3296 | 175 | 260 | 393 | 2.05 |

FIG. 8

STRUCTURE BASED ALIGNMENT AND CLUSTERING OF PROTEINS (STRALCP)

CROSS REFERENCE TO RELATED APPLICATION

This Application claims the benefit of Provisional Application No. 60/836,434 filed Aug. 7, 2006, the disclosure of which is hereby incorporated by reference, in its entirety.

STATEMENT REGARDING FEDERALLY FUNDED RESEARCH

The United States Government has rights in this invention pursuant to Contract No. W-7405-ENG-48 between the United States Department of Energy and the University of California, for the operation of Lawrence Livermore National Laboratory.

TECHNICAL FIELD

The disclosed embodiments generally relate to structural bioinformatics. Specifically, the disclosed embodiments relate to methods of clustering protein structures based on local and global structural similarity and identifying spans of conserved residues within the clustered proteins.

BACKGROUND

Protein structures are sets of solved atomic coordinates representative of a three dimensional structure of a protein. Atom coordinates may be solved computationally or experimentally using a variety of techniques such as x-ray crystallography, electron microscopy and nuclear magnetic resonance.

The Protein Data Bank (PDB, Berman et al. 2000, available at the website of the Research Collaboratory for Structural Bioinformatics) contains over 40,000 experimentally-solved protein structures and is growing at a rate of 500 entries per month. This rate of growth is expected to increase as technology and methodology for experimentally solving protein structures become more accurate and readily available.

The rapid growth of protein structure knowledge has increased the need for organization of experimentally-solved protein structures into families of protein structures by clustering or categorizing protein structures. When a new protein structure is solved, the determination of its cluster or family of homologous protein structures facilitates the rapid characterization of the function and properties of the newly-solved protein structure. The identification of families or clusters of protein structures also provides a definition of the set of homologous proteins from which to characterize conservation of the protein structures.

Structural bioinformatics approaches to clustering protein structures have largely been based on single metrics of similarity between protein structures. The generation of a single similarity metric is complicated by the fact that proteins have multiple structural domains as well as an overall ternary or quaternary structure. Approximately 40% of the protein structures in PDB have multiple domains (Redfern et al., 2005). Protein structural domains may be shared over evolutionarily unrelated structures and do not always confer functional properties. Hence, proteins with overall similarity in structure, herein referred to as global similarity, may not have good local correspondence between domains. Conversely, proteins that have a high degree of local similarity due to evolutionarily conserved domains may not always have good global similarity due to structurally variable or unstructured regions, such as loops.

Due to the complexity introduced by structural domains, structural bioinformatics approaches to protein classification that have relied upon a single metric of similarity have failed to provide accurate clustering of protein structures. In fact, the protein structures in the Structural Classification of Proteins database (SCOP, Murzin et al., 1995, available at the website of the Medical Research Council Laboratory of Molecular Biology), a classification of protein structures widely used in the art of structural bioinformatics, are classified by human curators through visual inspection of the protein structure models in conjunction with structural bioinformatics analyses.

Thus, there is a need in the art for improved methods of automatically clustering or categorizing protein structures. The present invention addresses these shortcomings of the prior art.

SUMMARY OF THE INVENTION

These needs are met by methods and computer program products for clustering a set of three dimensional protein structures.

Embodiments of the method comprise providing a structural alignment for a first protein structure and a second protein structure included in a set of protein structures. The method comprises determining a first plurality of fragments for the first protein structure, wherein each fragment comprises a pre-determined number of residues contiguous in the polypeptide sequence of the first protein structure. The method comprises determining a second plurality of fragments for the second protein structure, wherein each fragment comprises a pre-determined number of residues contiguous in the polypeptide sequence of the second protein structure. The method comprises generating a first plurality of pair-wise local homology values between the first plurality of fragments and the second plurality of fragments. The method further comprises determining that the first protein structure and the second protein structure form a first cluster of protein structures based on the plurality of pair-wise local homology values. The method further comprises storing the cluster of proteins.

In another aspect, the present invention may be embodied as a computer-readable storage medium on which is encoded computer program code for clustering a set of three dimensional protein structures according to the above described method.

The features and advantages described herein are not all-inclusive and, in particular, many additional features and advantages will be apparent to one of ordinary skill in the art in view of the figures and description. Moreover, it should be noted that the language used in the specification has been principally selected for readability and instructional purposes, and not to limit the scope of the inventive subject matter.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 7 illustrates STRALCP clustering applied to the same set of 20 structures as in FIGS. 4 and 6. STRALCP calculations were performed using default parameters (LGA_S=60%, DIST=5 Å).

FIG. 8 tabulates results from the evaluation of the differences between SCOP and STRALCP clusters at the level of SCOP families.

FIG. 10 illustrates a clustering of selected structures from the transferring SCOP family c.94.1.2 using a STRALCP multi-criteria clustering based on a default cutoff value LGA_S=60% (the iron-free apo form (Cluster 1) and the iron-binding holo form of transferrin (Cluster 2)). In column (c), FIG. 10 illustrates a clustering of selected structures from the transferring SCOP family c.94.1.2 using STRALCP clustering based on a high similarity value cutoff LGA_S=98%.

Figure 1:
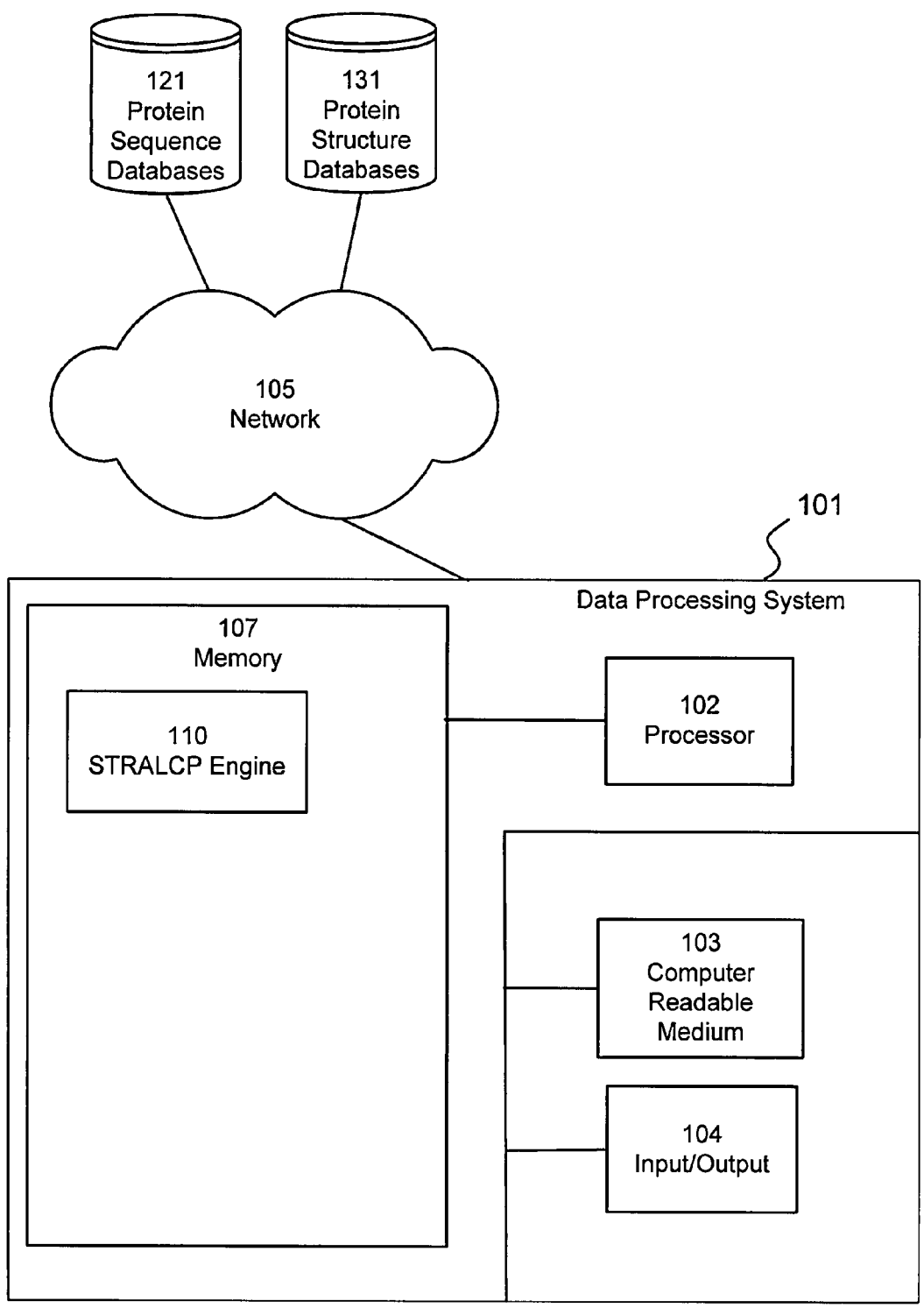
FIG. 1 shows a system architecture adapted to support one embodiment.

The figures depict various embodiments of the present invention for purposes of illustration only. One skilled in the art will readily recognize from the following discussion that alternative embodiments of the structures and methods illustrated herein may be employed without departing from the principles of the invention described herein.

DEFINITIONS

Residue: An amino acid residue is one amino acid that is joined to another by a peptide bond. Residue is referred to herein to describe both an amino acid and its position in a polypeptide sequence.

Polypeptide: A single linear chain of 2 or more amino acids. A protein is an example of a polypeptide.

Local Alignment: A local alignment is the identification of local similarities in an alignment or superposition of data. In reference to protein structure alignment, a local alignment refers to pairs of corresponding residues whose co-ordinate positions do not differ by more than a small number of Angstroms (e.g. 0.5 Angstroms) based on the superposition of their respective protein structures.

Global Alignment: A global alignment refers to the overall alignment or superposition of two sets of data. In protein structure alignment, metrics used to define global alignment include root mean square deviation (RMSD) or global distance test (GDT).

Contiguous residues: Contiguous residues are residues or pairs of residues which are sequentially contiguous in a polypeptide sequence, a sequence alignment or a structural correspondence.

Homolog: A gene related to a second gene by descent from a common ancestral DNA sequence. The term, homolog, may apply to the relationship between genes separated by the event of speciation or to the relationship between genes separated by the event of genetic duplication. Organisms which are un-related or distantly related though evolution may contain homologous sequences due to convergent evolution or targeted manipulation of their genetic material.

Conservation: Conservation is a high degree of similarity in the primary, secondary or ternary structure of molecules between homologs. This similarity is thought to confer functional importance to a conserved region of the molecule. In reference to an individual residue or amino acid, conservation is used to refer to a computed likelihood of substitution or deletion based on comparison with homologous molecules.

GDT Matrix: Distance matrices are used to present the results of the calculation of an optimal pair-wise alignment score. A GDT matrix is a type of distance matrix. In GDT matrices, the matrix field (i,j) is the score (number of residues superimposed under a given distance cutoff) assigned to the optimal alignment between two residues (up to a total of i by j residues) from the input structures. Each entry is calculated from the top-left neighboring entries by way of a recursive equation.

Substitution Matrix: A matrix that defines scores for amino acid substitutions, reflecting the similarity of physicochemical properties, and observed substitution frequencies. These matrices are the foundation of statistical techniques for finding alignments.

DETAILED DESCRIPTION OF THE DRAWINGS

Embodiments are now described with reference to the figures where like reference numbers indicate identical or functionally similar elements.

FIG. 1 shows a system architecture adapted to support one embodiment of the STRALCP Engine 110. The system architecture includes a network 105, through which any number of Protein Structure Databases 131 and Protein Sequence Databases 121 are accessed by a data processing system 101.

FIG. 1 shows component engines used to cluster protein structures. The data processing system 101 includes the STRALCP Engine 110. Each of the foregoing is implemented, in one embodiment, as software modules (or programs) executed by processor 102.

The STRALCP Engine 110 operates to import and/or generate a set of protein structures by accessing the Protein Sequence Databases 121 and Protein Structure Databases 131 through the network 105 (as operationally and programmatically defined within the data processing system).

It should also be appreciated that in practice at least some of the components of the data processing system 101 will be distributed over multiple computers, communicating over a network. For example, the STRALCP Engine 110 may be deployed over multiple servers. As another example, the STRALCP Engine 110 may be located on any number of different computers. For convenience of explanation, however, the components of the data processing system 101 are discussed as though they were implemented on a single computer.

In another embodiment, some or all of the Protein Sequence Databases 121 and the Protein Structure Databases 131 are located on the data processing system 101 instead of being coupled to the data processing system 101 by a network 105. For example, the STRALCP Engine 110 may import protein sequence from Protein Structure Databases 131 that are a part of, or associated with, the data processing system 101.

FIG. 1 shows that the data processing system 101 includes a memory 107 and one or more processors 102. The memory 107 includes the STRALCP Engine 110 which is preferably implemented as instructions stored in memory 107 and executable by processor 102.

FIG. 1 also includes a computer readable storage medium 103 for storing executable code, for example the STRALCP Engine 110. FIG. 1 also includes one or more input/output devices 104 that allow data to be input and output to and from the data processing system 101. It will be understood that embodiments of the data processing system 101 also include standard software components such as operating systems and the like and further include standard hardware components not shown in the figure for clarity of example.

Figure 2:
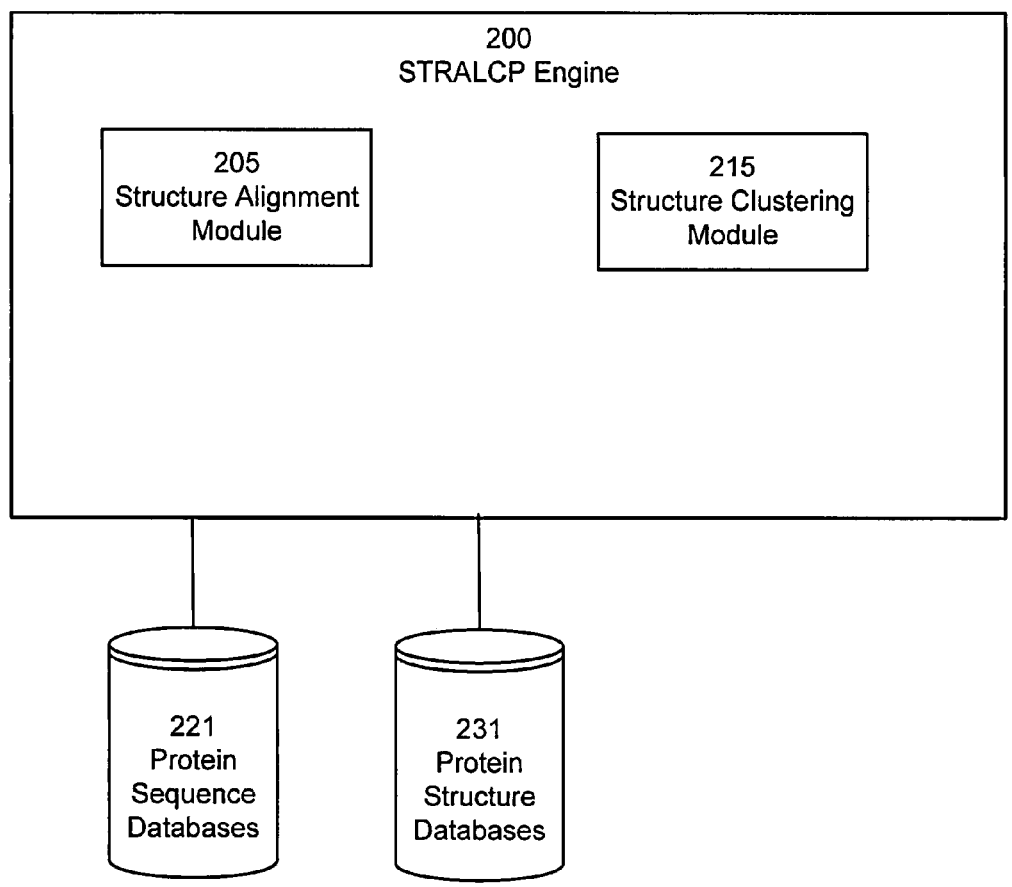
FIG. 2 illustrates the STRALCP engine according to one embodiment.

FIG. 2 illustrates one embodiment of the STRALCP Engine 200. The STRALCP Engine 200 functions to cluster a set of protein structures. The STRALCP Engine 200 is adapted to import protein structures from Protein Structure Databases 231 such as Protein Data Bank (PDB, available at the website of the Research Collaboratory for Structural Bioinformatics). The STRACP Engine 200 is adapted to communicate with Protein Sequence Databases 221 such as MvirDB (Zhou et al. NAR) or GenBank (available at the website of the National Center for Biotechnology Information).

The STRALCP Engine 200 consists of two modules, a Structure Alignment Module 205 and a Structure Clustering Module 215. The functions of the engines discussed herein are separated into modules for purposes of discussion only. Different embodiments of the present invention may distribute functions among modules in different ways.

Protein Structure Alignment

The Structure Alignment Module 205 functions to generate protein structure alignments between protein structures. Methods of solving protein structure are discussed below in the section titled Protein Structure Modeling. The Structure Alignment Module 205 takes as input a set of protein structures identified for clustering. The set of protein structures may be identified by user input or as output of another program. The Structure Alignment Module 205 is adapted to import protein structures directly from the Protein Structure Databases.

The Structure Alignment Module 205 generates protein structure alignments by determining the optimal residue-residue correspondence between protein structures. The optimal residue-residue correspondence is computed by computationally aligning or superimposing the sets of spatial co-ordinates defining points representing each residue (e.g. alpha carbon (Calpha)atoms) that form the protein structures in order to minimize distance between the spatial co-ordinates of the sets of atoms. Typically, the sets of spatial-coordinates represent the alpha carbon backbone of the two protein structures but structure alignments may also incorporate spatial co-ordinates of other atoms such as side chain atoms or other sets of spatial co-ordinates representing each residue.

According to one embodiment of the present invention, the Structure Alignment Module 205 uses a variety of methods and metrics for generating an optimal set of correspondences. The Structure Alignment Module 205 calculates the root mean square deviation (RMSD) of all the corresponding alpha carbon atoms in the backbone. The Structure Alignment Module 205 further calculates the number of equivalent or structurally aligned residues.

In some embodiments, the Structure Alignment Module 205 calculates distance matrices such as GDT matrices in order to generate an optimal set of correspondences. Alternatively, the Structure Alignment Module 205 generates the optimal set of correspondences by maximizing the number of equivalent residues while RMSD is kept close to a constant value.

In the generation of the set of correspondences, various cutoff values can be specified to increase or decrease the stringency of the alignment or super-position. These cutoffs can be specified using distance in Angstroms. Depending on the level of stringency employed in the present invention, the distance cutoff used is selected from a range of 0.5 to 10.0 Angstroms. In a specific embodiment, the cutoff may have default value of 5.0 Angstroms. One of ordinary skill will recognize that the utility of stringency criterion depends on the resolution of the structure determination.

In another embodiment of the present invention, the Structure Alignment Module 205 generates the set of residue-residue correspondences using a local-global alignment (LGA), as described in US Patent Application Number 2004/0185486. In this method, a set of local superpositions are created in order to detect regions of the protein structures that are most similar.

LGA uses the LGA_S scoring function to determine local and global similarity in determining the optimal superposition or alignment between two protein structures. The LGA_S scoring function has two metrics, LCS (longest continuous segments) and GDT (global distance test), defined for the detection of regions of local and global structure similarities between analyzed structures. In comparing two protein structures (e.g., M-model and T-target), the LCS procedure localizes and superimposes the longest segments of residues that can fit under a selected set of RMSD cutoffs. The GDT algorithm is designed to complement evaluations made with LCS searching for the largest (not necessary continuous) set of "equivalent" residues that deviate by no more than specified distance cutoff.

Let:

m—the number of residues in M structure, t—the number of residues in T structure, $R(r)=100/t*L(r)$, where $L(r)$ is the length of the identified longest continuous segment of M:T residue pairs that fits under r Å of RMSD cutoff, X—the set of all M:T superpositions calculated by LGA algorithm, $G(s, d)$—the number of M:T residue pairs for which the distance between Calpha (Alpha carbon) atoms is not greater than d Å after the superposition $s \in X$ is applied, $D(d)=100/t*\max\{G(s,d): s \in X\}$ is the maximal detected percentage of Ca atoms in T structure that are within a distance threshold of d Å from M structure upon calculated $s \in X$ superpositions.

The LGA_S structure similarity scoring function is defined as a function of two structures. M and T calculated as a combination of R(r) results from LCS calculations using the set of n RMSD cutoffs r (e.g., n=3; r=1.0, 2.0, 5.0), and D(d) results from GDT calculations using the set of k distance cutoffs d (e.g., k=20; d=0.5, 1.0, . . . , 10.0):

$$LGA\_S(M, T)=(1-w)*S(LCS(M, T))+w*S(GDT(M, T)),$$

where $$S(LCS) = \frac{2}{n \cdot (n+1)} \sum_{j=1}^{n} (n-j+1) * R(n), n = 3, n = 1.0, 2.0, 5.0,$$

$$S(GDT) = \frac{2}{k \cdot (k+1)} \sum_{j=1}^{k} (k-j+1) * D(d_j), k = 20, d_j = 0.5, 1.0, \ldots, 10.0,$$

and w=0.75 is a parameter (0<=w<=1) representing a weighting factor between LCS and GDT results.

STRALCP

The Structure Clustering Module 215 functions to cluster a set of protein structures based on the generated protein structure alignment. The Structure Clustering Module 215 is adapted to receive protein structure alignment data from the Structure Alignment Module 205.

The Structure Clustering Module 215 also functions to generate values representative of the local and global similarity of protein structures based on the received protein structure alignment. The Structure Cluster Module 215 generates values based on a pre-defined scoring function. A scoring algorithm is defined to take into account a number of similarity characteristics of the compared protein structures such as global alignment score local alignment score, and other characteristics that can be derived from the structural alignment such as level of sequence identity observed in local pair-wise alignments. Suitable local alignment scores include length of local pair-wise alignments and the RMSD of the local pair-wise alignment. Suitable global alignment scores include LGA_S value, number of superimposed residues under a selected distance cutoff, the RMSD value calculated on all aligned residues and the distribution of structurally conserved regions in the protein structures. It is expected that other suitable global and local alignment scores will be apparent to those skilled in the art.

Depending on the goal of the clustering, the Structure Clustering Module 215 selects one characteristic or combines different similarity characteristics to generate values representative of the local or global similarity of two protein structures. The Structure Clustering Module 215 generates a single value or multiple values based on the different similarity characteristics. Additionally, scores representative of the similarity of two protein structures may be assigned to fragments of the protein structures. Specific embodiments of suitable scoring functions are discussed in detail with respect to FIG. 3.

The Structure Clustering Module 215 also functions to cluster the set of protein structures based on one or more of the generated values. In some embodiments, the Structure Clustering Module 215 clusters proteins into groups based on user defined thresholds for the generated scores. Conventional methods of clustering into groups based on one or more values representative of similarity such as hierarchical agglomerative clustering or recursive partitioning are also used by the Structure Clustering Module 215. According to the embodiment, the Structure Clustering Module 215 may perform one clustering of the protein structures based on one value or set of values or perform multiple sequential clusterings of the protein structures based on the multiple generated values. Suitable methods of clustering the set of protein structures based on pair-wise scores are discussed below with respect to FIG. 3.

Figure 3:
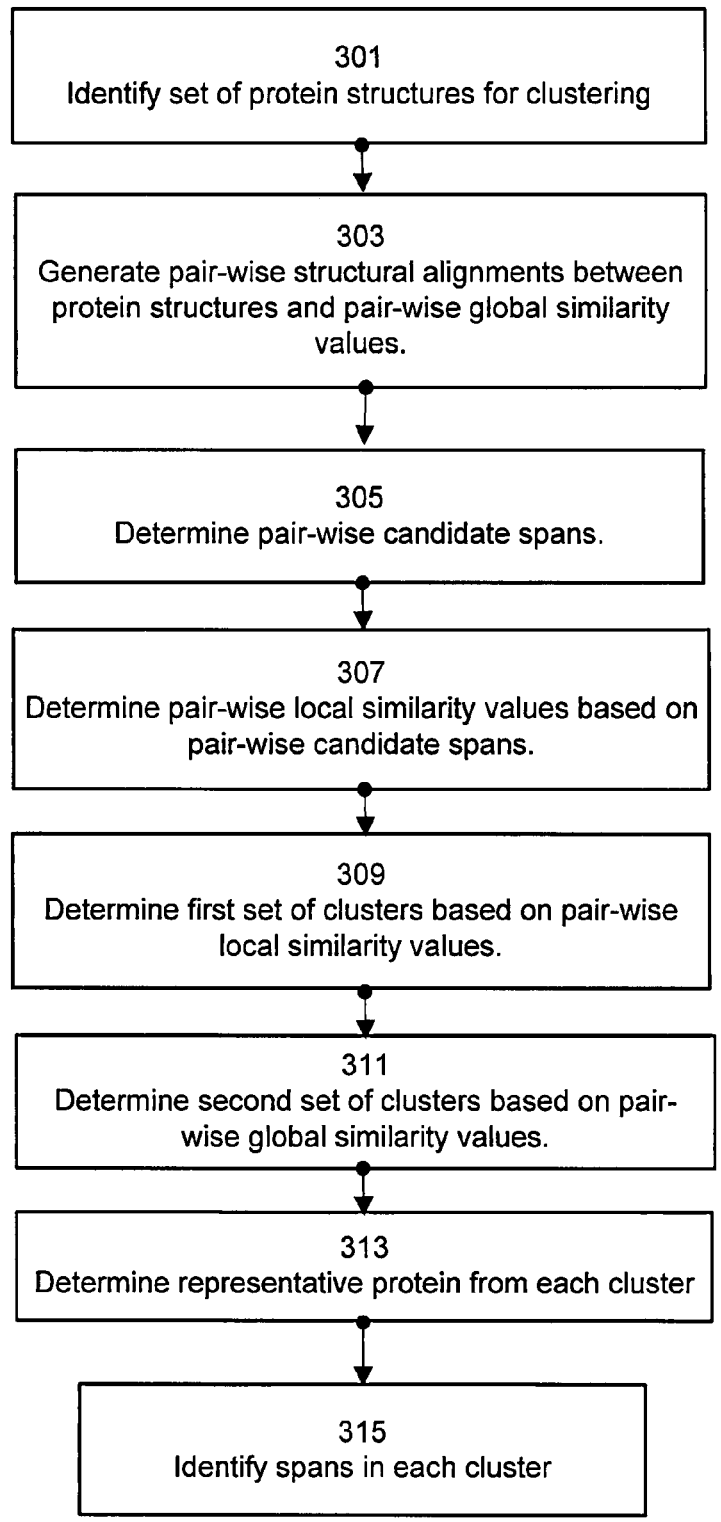
FIG. 3 shows a high level workflow of the STRALCP engine according to one embodiment.

FIG. 3 illustrates a high level overview of protein structure clustering using the STRALCP Engine 200. The Structure Alignment Module 205 initially identifies 301 a set of proteins for clustering. According to this embodiment, the set of protein structures may be specified by the user or may be selected based on any criteria such as homology or annotation in a protein sequence database.

The Structure Alignment Module 205 generates 303 pair-wise structure alignments between the identified protein structures. In one embodiment, the Structure Alignment Module 205 uses the above described Local Global Alignment (LGA) program to generate 303 the pair-wise structural alignment between all identified protein structures. Other embodiments may employ different methods of generating a global alignment, a local alignment or any combination thereof. In embodiments in which a global alignment is generated, a maximum distance between residues in the structural alignment is a specified. This distance ranges from 0.5 to 10.0 Angstroms. In a specific embodiment, the pre-determined distance is set to a default value of 5.0 Angstroms.

The Structure Clustering Module 215 determines 305 pair-wise candidate spans of contiguous residues based on the generated pair-wise structural alignment. A span is defined as a contiguous plurality of pairs of residues from two protein structures whose alpha carbon co-ordinates (or any other set of spatial co-ordinates used to represent each residue) are within a pre-determined distance from each other in the structure alignment.

The Structure Clustering Module 215 determines 305 pair-wise candidate spans based on a threshold length of contiguous residues such as 3, 4, 5, or 6 contiguous residues. According to the embodiment, the Structure Clustering Module 215 determines 305 the pair-wise candidate spans based on a pre-determined distance between residues in a local alignment calculated using root mean square deviation in a local window of residues. According to the embodiment, the pre-determined distance may be calculated using a root mean square deviation based on different sized windows surrounding a given pair of residues in the pair-wise protein structure alignment, for instance windows of 3, 4, 5 or 6 residues. Those skilled in the art will note the utility in adjusting threshold parameters for both the length and the threshold distance between residues in determining candidate spans.

In a specific embodiment, the Structure Clustering Module 215 determines 305 pair-wise candidate spans of at least 5 contiguous residues in the pair-wise structure alignment that are superimposed in a global alignment within a distance cutoff of 5.0 Angstroms, and locally with RMSD cutoff of 0.5 Å. The RMSD between individual residues is calculated using a 3-residue-long window.

The Structure Clustering Module 215 determines 307 a plurality of pair-wise local similarity values based on the pair-wise candidate spans. In one embodiment, pair-wise local similarity values are based on a set of fragments that are determined for each structure. The Structure Clustering Module determines a set of fragments for each protein structure, each fragment formed of a set of residues that are contiguous in the polypeptide associated with the protein structure. In one embodiment, the set of fragments are sequential and defined by splitting the corresponding amino-acid sequence into consecutive n-residue-long sub-sequences. In a specific embodiment, the number of contiguous residues is 10 (i.e. n=10 and a 120-residue-long protein comprises 12 fragments).

The Structure Clustering Module 215 determines 307 a plurality of pair-wise local similarity values, which indicate whether two pair-wise fragments between two protein structures share a candidate span. Each fragment that does not share a span with a protein structure in a pair-wise comparison is herein referred to as an "empty fragment". According to the embodiment, the pair-wise local similarity values can be represented in different ways. In one embodiment, the pair-wise local similarity values can be represented as binary or absolute value indicating whether or not a pair of fragments share a candidate span or are empty fragments (e.g. 1 for a shared span, 0 for an empty fragment). Alternatively, the pair-wise local similarity value may be represented as a numeric value indicating the number of residue pairs within two fragments that are in one or more candidate spans. The numeric value can be a number of residue pairs within two fragments that are in a candidate span or a percentage of the residues in the fragments that form residue pairs in a candidate span. Empty fragments would be assigned a value of nil or zero.

The Structure Clustering Module 215 determines 309 a set of clusters based on the pair-wise local similarity values. In a specific embodiment, a list of protein structures that have at least a pre-determined number of fragments having pair-wise local similarity values that indicate that the two fragments share a set of spans is generated for each protein structure. In a specific embodiment, the list of protein structures is limited to protein structures for which 80% of the fragments in both protein structures share a span or are "non-empty." The Structure Clustering Module 215 uses the lists of non-empty fragments to determine 309 an initial maximal cluster of protein structures wherein each pair of protein structures have 80% of their fragments share a candidate span (i.e. are non-empty).

The Structure Cluster Module 215 determines 311 a second set of clusters based on the pair-wise global similarity values between protein structures. Pair-wise global similarity values are generated as part of the structural alignment to represent the overall or global similarity between the alpha carbon backbones of two protein structures. According to the embodiment, pair-wise global similarity values can be any suitable value to measure the overall similarity between proteins, such as root mean square deviation (RMSD) or global distance test (GDT). Other appropriate values to measure global similarity will be apparent to those skilled in the art. In embodiments in which LGA is used to determine structural alignment, LGA_S values are calculated as pair-wise global similarity values.

In determining 311 the second set of clusters, the Structure Cluster Module 215 uses the global pair-wise similarity values to determine that the clusters of proteins from the initial clustering have good pair-wise global similarity values. In one embodiment, the Structure Cluster Module identifies pair-wise global similarity values between protein structures in a cluster and reassigns protein structures to different clusters if the pair-wise similarity values between a pair of the protein-structures is below a certain value. In a specific embodiment, the Structure Cluster Module 215 uses a cutoff of 60% global similarity based on an LGA_S score.

In re-assigning the protein structures to different clusters to determine 311 the second set of clusters based on the pair-wise global similarity values, the Structure Cluster Module 215 seeks to minimize the number of clusters necessary to assign each protein structure in the identified set of protein structures to a cluster. According to the embodiment, the Structure Cluster Module 215 is provided values specifying a pre-determined minimum and maximum number of clusters to form, the values ranging from one cluster to the number of given protein structures. According to the embodiment, the resulting number of clusters is determined by the Structure Cluster Module 215 as a minimum number of clusters needed to distribute all given protein structures and satisfy the threshold values of percentage of non-empty fragments and global alignment values.

The Structure Cluster Module 215 determines 313 a representative protein structure from each cluster. The representative protein structure is the protein structure that has the highest local and global similarity to each other protein structures in the cluster as defined by the pair-wise local similarity values. The Structure Cluster Module 215 generates for each protein structure in a cluster, a list of all pair-wise local and global similarity values. The Structure Cluster Module 215 selects the protein structure in each cluster that has the highest pair-wise local and global similarity values as the representative structure. According to the embodiment, the pair-wise local and global similarity values may be assigned different weighting schemes in calculating the representative cluster. Those skilled in the art will readily note the utility in different weighting schemes. In a specific embodiment, the protein structure that has the largest number of non-empty fragments, the highest LGA_S value with other members of the cluster, and the highest number of residues in calculated spans is selected as the representative protein structure.

The Structure Cluster Module 215 then identifies 315 a set of spans for each identified cluster based at least in part on the plurality of pair-wise candidate spans. For each identified cluster, pair-wise candidate spans are combined to form common spans of the set of residues which are conserved between all structures within the cluster or family of protein structures. The Structure Cluster Module 215 may identify 315 spans by performing another structural alignment such as a Local Global Alignment or by combining the correspondences generated in the pair-wise structural alignments. The degree of structural homology may differ between different pairs of protein structures within a cluster. Therefore, not all pair-wise candidate spans are necessarily incorporated into the representative set of spans for each given cluster.

Once the clustering has been completed and representative protein structures have been selected, the set of representative protein structures are used to assign newly-solved protein structures to respective clusters. In one embodiment, the Structure Alignment Module 205 performs a structural alignment between newly-solved protein structure and each representative protein structure for each cluster. The structural alignment may be a global alignment, a local alignment or any combination thereof. The Structure Clustering Module 215 generates a pair-wise local similarity value, a pair-wise global similarity value or any suitable similarity value to compare the newly-solved protein structure to each representative protein structure for each cluster. Other suitable similarity values for comparing the newly-solved protein structure to each representative structure will be readily recognized by those skilled in the art.

The Structure Clustering Module 215 then assigns a protein structure to one of the clusters based on the generated similarity values. For example, the newly-solved protein structure will be assigned to the cluster for which it has the highest similarity value in comparison to the representative protein structure. According to the embodiment, the Structure Clustering Module 215 may use one or more threshold similarity values in assigning the protein structure to a cluster in order to ensure that similarity values are above a threshold similarity before assigning a protein structure to a cluster. In a specific embodiment, a minimum global similarity value of 60% is used. Other embodiments may include the use of pair-wise local similarity values that indicate whether fragments generated for a newly-solved protein structure and each representative protein structure contain candidate spans as discussed with respect to step 307.

Working Example

Through structural comparison and classification, a family of crystal protein structures was identified that failed to be detected by sequence-based methods such as PSI-BLAST (Atschul et al., 1997). Using a structure-based method (e.g. DALI, LGA) it was found that three EAP domains from Staphylococcus aureus (Geisbrecht et al., 2005), which could not be properly classified by sequence-based methods, shared a previously unrecognized similarity to another class of bacterial toxins.

Structure-based Alignment and Clustering of Proteins (STRALCP), is presented herein as applied to these domains. For each of the EAP domains (Eap2 (PDB entry: 1yn3), EapH1 (PDB entry: 1yn4), EapH2 (PDB entry: 1yn5)), structural PDB searches were performed using a Local Global Alignment (LGA) server (Zemla et al. 2005). Resultantly, 134 domains from the SCOP superfamily d.15.6 (Superantigen toxins, C-terminal domain) were identified as most similar to EAP structures. In provided FIGS. 4, 6, and 7 only 20 structures are shown; 3 EAP domains and 17 domains from SCOP superfamily d.15.6. In general, all EAP domains demonstrated a high level of overall structure similarity (LGA_S over 60%) to most of the structures from SCOP superfamily d.15.6, whereas the level of sequence identity was very low (below 20%).

Figure 4:
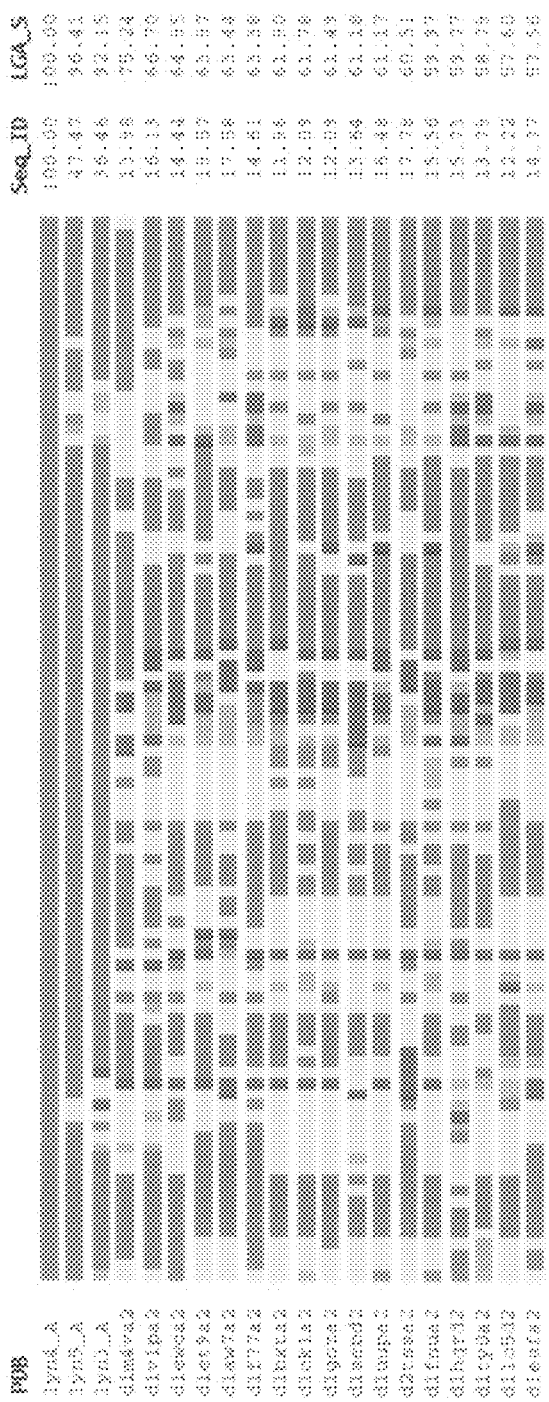
FIG. 4 illustrates a protein structure alignment between EAP domains from *S. aureus* (PDB: 1yn3, 4, and 5) and 17 protein domains from the SCOP superfamily comprising superantigen toxins.

FIG. 4 illustrates a protein structure alignment between the EAP domains from *S. aureus* (PDB: 1yn3, 4, and 5) and 17 protein domains from the SCOP superfamily d.15.6 comprising superantigen toxins. All protein structures were compared to the structure of EapH1 (1yn4_A, at top), which serves as a frame of reference. Colored bars represent Calpha-Calpha distance deviation between 1yn4_A (99 residues; from the left (N terminal) to the right (C terminal)) superimposed with 20 structures from PDB (first bar represents a 1yn4_A-1yn4_A self-comparison). Colors represent distances between aligned residues and range from green (below 2 Å) to red (above 6 Å). The columns at the right contain information about the level of sequence identity (Seq_ID) and structure similarity (LGA_S).

Figure 5:
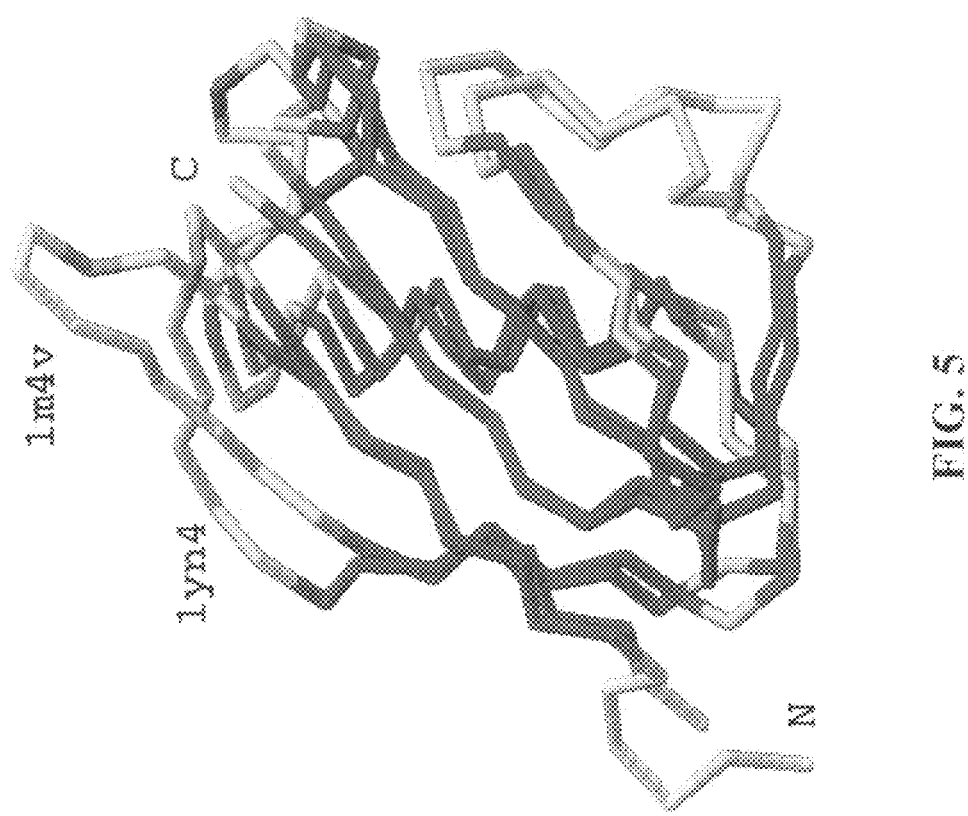
FIG. 5 depicts a 3D plot of structural superposition between 1yn4_A and 1m4v_A (SCOP domain: d1m4va2).

FIG. 5 depicts a 3D plot of structural superposition between 1yn4_A and 1m4v_A (SCOP domain: d1m4va2) that corresponds to the fourth colored bar from the top in FIG. 4. The protein structure is formed by 4 strands and 1 helix. The superposition of 1yn4_A and d1m4va2 (labeled as 1m4v_A in FIG. 5) corresponds to the fourth bar in FIG. 4 and shows that these two structures differ in several loop regions only (structural deviations above 2A are colored in yellow-red). The level of sequence identity between proteins Seq_ID is approximately 14%, and the level of structure similarity LGA_S is approximately 75%.

Figure 6:
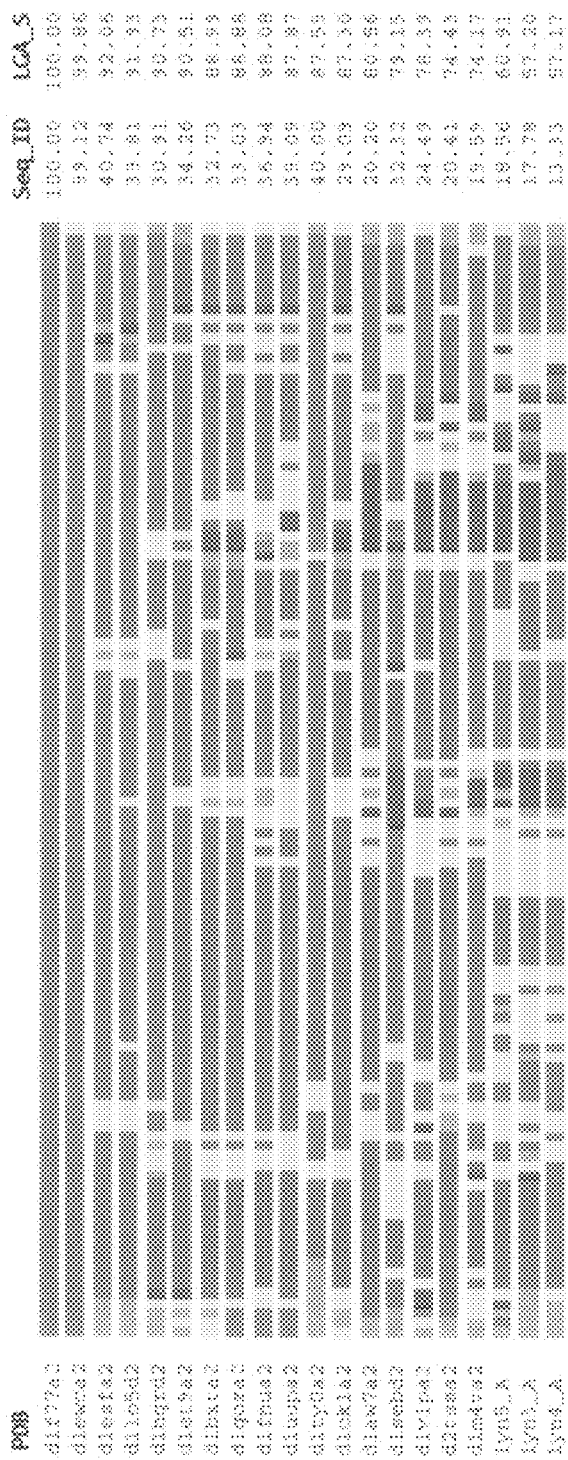
FIG. 6 illustrates a structural alignment between EAP protein structure domains from *S. aureus* and protein structures from the SCOP superfamily of superantigen toxins containing the same domains as in the alignment illustrated in FIG. 4.

FIG. 6 illustrates a structural alignment between EAP protein structure domains from *S. aureus* and protein structures from the SCOP superfamily of superantigen toxins containing the same domains as in the alignment illustrated in FIG. 4. In FIG. 6, SCOP domain d1f77a2 (Hakansson et al., 2000) serves as a frame of reference for this comparison. The coloring scheme is the same as in FIGS. 4 and 5.

From the comparison of the two plots illustrated in FIGS. 4 and 6, it is apparent that d1f77a2 may serve as a better representation (average structure) for the analyzed set of 20 proteins (at least for the top 13 of them) than the structure 1yn4_A. The obtained results in FIGS. 2 and 6 suggest that a given set of 20 structures can be structurally divided into at least two clusters.

FIG. 7 illustrates clustering of the same set of 20 structures as in FIGS. 4 and 6 performed using the STRALCP Engine 200. In this embodiment, the STRALCP Engine 200 used LGA to generate pair-wise structural alignments between each protein structure in fold a.8 using a maximum distance of 5 Angstroms between residues to generate the pair-wise global superpositions. Candidate spans of a minimum of 5 contiguous residues were identified from each pair-wise structural alignment using a predetermined distance of 5 Angstroms of calculated root mean square deviations using a window size of 3 residues. Sequential fragments 10 residues in length were determined for each protein structure from fold a. 8. Pair-wise local similarity values indicating whether pairs of fragments shared candidate spans were calculated. An initial clustering was performed using a cutoff value of 80% non-empty fragments between each protein structure in each cluster. A second and final clustering was performed by applying a cutoff value of 60% global structure similarity to LGA_S scores generated for the pair-wise structural alignments.

In FIG. 7, each row begins from the cluster number, followed by the domain name, and the set of amino-acids that are extracted from detected structurally conserved spans. Dots indicate regions that structurally deviate in at least one pair-wise comparison between members of the cluster. Note: dots do not indicate the actual number of residue pairs between detected spans. They are introduced for formatting purposes only.

In clustering illustrated in FIG. 7, the EAP structures: 1yn3-5 are grouped together (Cluster2) with four other protein structures: SET1 (PDB: 1v1p) [21], SET3 (PDB: 1m4v) (Arcus et al. 2002), and TSST1 (PDB: 1aw7, 2tss) (Earhart et al.,1998, Prasad et al., 1997). Additional tests showed that had more stringent global similarity requirements (e.g., LGA_S cutoff 80%) been introduced, then Cluster2 would have been split into two additional clusters where all three EAP domains (1yn3-5) were separated from the SET1, SET3, and TSST1 structures.

Benchmark Test

A comparison of STRALCP classification with SCOP classification was performed as a benchmark test. In the comparison with SCOP, STRALCP calculations were performed for 3,296 SCOP domains classified within 20 different folds. These calculations are tabulated in FIG. 8. In order to evaluate the accuracy of our clustering approach, we estimated the differences between SCOP and STRALCP clustering (for example on the level of SCOP families) by introducing the following measure of misclustering effect (MC). Let:

Nc—the number of created clusters

Cf(i)—the number of different families clustered together within the i cluster,

The score indicating the misclustering effect MC (when domains from different SCOP families are grouped together) can be calculated from the formula:

$$MC = \left(1.0 - \frac{1}{Nc}\sum_{i=1}^{Nc}\frac{1}{Cf(i)}\right) * 100.0$$

The range of this measure is 0.0<=MC<100.0, and 0.0 indicates a perfect clustering (i.e., agreement with SCOP classification).

The MC measure allows the comparison of different clustering schemes by their agreement in separating proteins from different clusters. The goal of this measure is not to calculate how many domains are clustered differently, but of how many the created clusters are compromised. That is, how many of the created clusters contain proteins that are separated in another clustering scheme.

FIG. 8 tabulates the results from applying MC formula to the clusters calculated on a randomly selected set of 20 SCOP folds that consist of multiple superfamilies and families (Ns=175 superfamilies, Nf=260 families, and Nd=3,296 domains). Here Nd—number of domains within the fold, Ns=number of superfamilies, Nf=number of families, Nc=number of created clusters and MC=misclustering effect calculated.

The analysis of the results provided in FIG. 8 demonstrates that the STRALCP algorithm, even if it is purely based on structure comparisons, exhibits a low (below 10%) MC effect: domains from different SCOP families were clustered separately.

Figure 9:
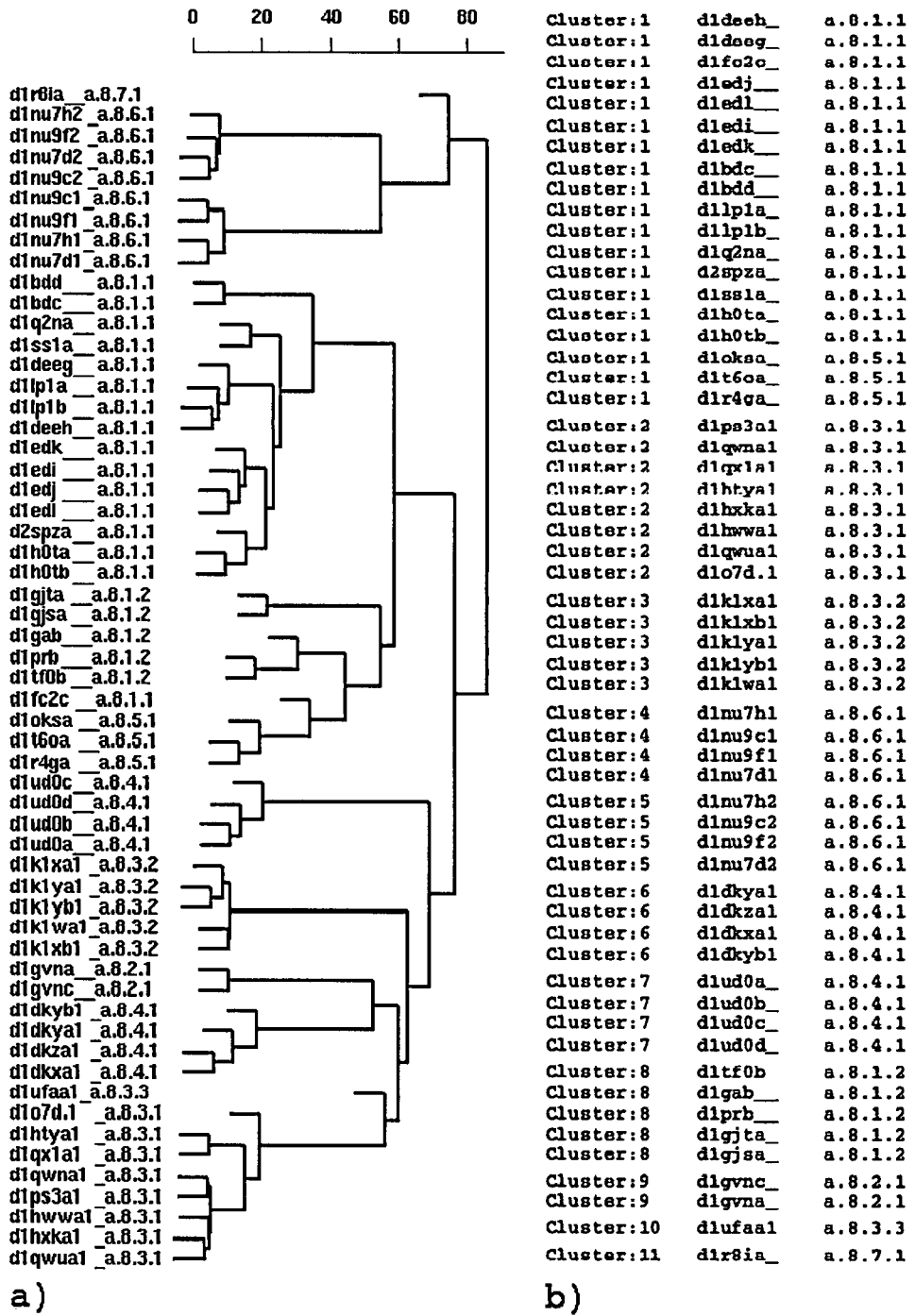
FIG. 9a illustrates a dendrogram representing the results of a clustering of SCOP domains from SCOP fold a.8 based on the single measure of LGA_S score.
FIG. 9b illustrates a clustering of SCOP domains from SCOP fold a.8 using the STRALCP Engine.

The STRALCP algorithm is able to detect the structural differences between domains from the same SCOP family and cluster them separately. FIG. 9a illustrates a dendrogram representing the results of a clustering of SCOP domains from SCOP fold a.8 based on the single measure of LGA_S score. Each code (entry_family) represents one protein from the SCOP classification: entry and family number.

FIG. 9b illustrates a clustering of the structures from the fold a.8, which can be clustered automatically using the STRALCP (multi-criteria based clustering) Engine 200. In this embodiment, STRALCP was performed using LGA to generate pair-wise structural alignments between each protein structure in fold a.8. Candidate spans of a minimum of 5 contiguous residues were identified from each pair-wise structural alignment using a maximum distance of 5 Angstroms for calculated the global superposition, and as a pre-determined distance of 5 Angstroms for local superpositions calculated using root mean square deviation with a window size of 3 residues. Sequential fragments 10 residues in length were determined for each protein structure from fold a. 8. Pair-wise local similarity values indicating whether pairs of fragments shared candidate spans were calculated. A first clustering was performed using a cutoff value of 80% non-empty fragments between each protein structure in each cluster. A second and final clustering was performed using a cutoff value of 60% global structure similarity LGA_S.

In the far right column of FIG. 9b SCOP family codes are provided in association with the cluster assignment and structure identifier. As seen by the correspondence between the SCOP family codes and the clusters, this example demonstrates that by using STRALCP we can clearly separate proteins into appropriate clusters that correspond with a high agreement to the defined SCOP families FIG. 9b also demonstrates the ability of the STALCP approach to identify structural differences within a SCOP family and create sub-clusters according to these differences. In FIG. 9b the family a.8.6. 1 is separated by STRALCP into two clusters: cluster 4, which corresponds to the first domain of *Staphylocoagulase aureus* and cluster 5 which corresponds to the second domain of *Staphylocoagulase aureus*. The family a.8.4.1 was divided into two clusters: cluster 6 which corresponds to the DnaK domain from *Escherichia coli* and cluster 7 which correspond to the DnaK domain from *Rattus norvegicus*. In purely structure-based classifications such additional separation can also be observed when different conformations of the same multi-domain structure (e.g., "open" and "closed" versions of the same protein) are clustered together in SCOP. In such cases, STRALCP would group the domains in different clusters. We consider this ability a beneficial one to the developed STRALCP approach.

It provides valuable information about the regions that are structurally in the same conformation, which could be useful in various studies and classification schemes. The separation of similar or identical proteins, but in different structural conformations, could be reduced by introducing a sequence similarity analysis into the STRALCP algorithm.

Figure 10:
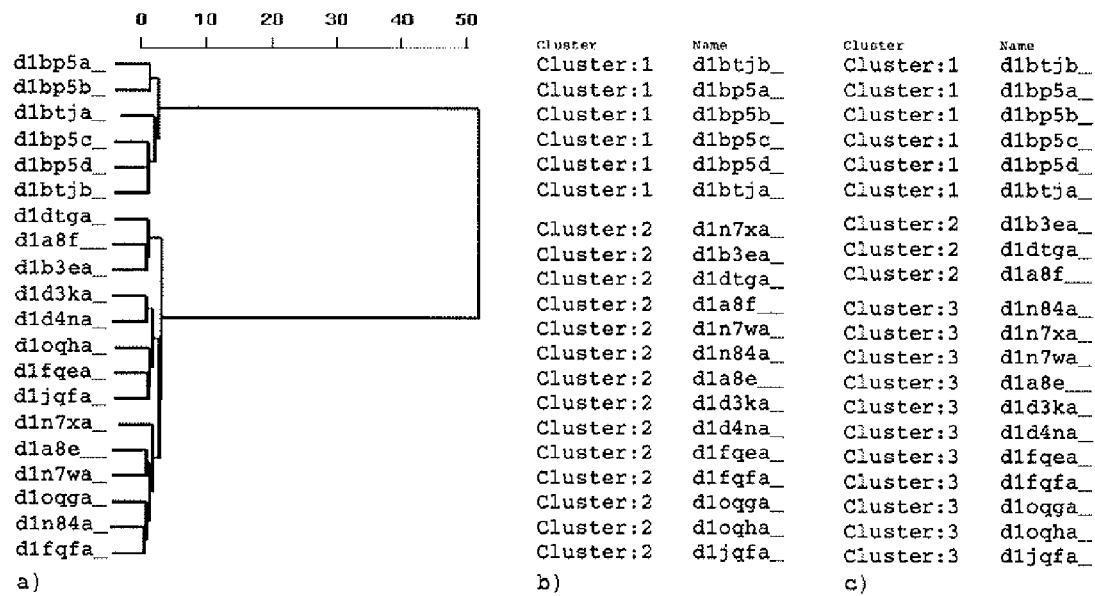
FIG. 10 illustrates in column (a) a clustering of selected structures from the transferring SCOP family c.94.1.2 using a single measure based clustering (dendrogram for hierarchical clustering) using structure similarity scoring function $LGA_{13}$ S. In column (b)

In FIG. 10, a clustering of selected structures from SCOP family c.94.1.2 is shown. Column (a) shows the dendrogram of the clustering created using LGA_S as a single scoring function. Columns (b) and (c) show the results from a multi-criterion STRALCP clustering. The LGA calculations were performed with the distance cutoff DIST=1.0Ångstroms, and the results of the clustering corresponded to the results reported by the STRuster method.

A limitation of the STRuster method is its applicability only to the set of alternative structures for a single given protein. This means that in the STRuster algorithm the residue-residue correspondences in analyzed structures are already known, so the RMSD calculations can be performed easily. STRALCP starts from structure alignment calculations performed by LGA, which determines residue-residue correspondences between proteins de novo, so any set of protein structures can be automatically classified without any prior knowledge of sequence correspondence.

Experiments indicate that LGA_S serves well as a single measure scoring function to evaluate the overall level of structure similarity and to allow an initial grouping and structural clustering of proteins.

For the hierarchical clustering of calculated LGA_S results from all-against-all structure comparisons, a language and programming environment for statistical computing and graph programming called R was used (R, version 2.1.1). Provided dendrograms were generated for visualization of the hierarchical dependences in the calculated examples.

Another requirement for clustering algorithms is that they calculate the optimal number of clusters where the entries can be grouped in a robust way. In the STRuster method, the resulting similarity value M(a,b) is used as input for two alternative clustering methods: hierarchical clustering and partitioning around medoids (PAM). The silhouette width value is a measure of cluster validity and is used to select the best number of clusters obtained with the PAM algorithm. Hierarchical clustering reflects the hierarchy of similarities between all pairs of models, while PAM groups the models into the optimal number of clusters.

Unlike the approaches described above, where the clustering and the calculation of the optimal number of clusters are based on a single structure similarity scoring function, the STRALCP algorithm uses a combination of distinct numerical criteria. In STRALCP, an optimal number of clusters is determined by grouping models according to their overall similarity (LGA_S) combined with information about local similarities in detected structurally conserved frames (spans).

There are three important objectives in the automation of structure classification: (1) the calculation of an optimal (based on given criteria) number of clusters, (2) the selection of a representative structure, and (3) the assignment of analyzed structures to the resulting clusters. In the STRALCP algorithm these objectives are achieved by applying several numerical criteria that reflect not only the overall level of similarity between compared structures (e.g., LGA_S score), but also explore information about their similarity in different structural regions, such as in the detected structurally conserved frames.

Various embodiments of the method include the following steps:
1. LGA is used to perform an all-against-all comparison in which, for a given set of structures, each structure is used as a frame of reference in a comparison against all others.
2. Every frame of reference is assigned a set of sequential fragments, which are defined by splitting the corresponding amino-acid sequence into consecutive n-residue-long sub-sequences (n =10 is used as a default parameter; e.g., a 120-residue-long protein comprises 12 fragments).
3. After we perform an all-against-all structure comparison (step 1) the following information is assigned to each frame of reference:
   a. LGA_S values between the frame of reference and each other structure
   b. The number of residue pairs that are superimposed locally within RMSD cutoff 0.5 Å. Continuous structural segments formed by such residue pairs that are at least five residues long are marked as candidate spans
   c. The number of non-empty fragments, i.e., sequential fragments that overlap by at least one residue with at least one detected span in compared structures
4. An initial grouping of structures is done by assigning a list of proteins that have at least 80% (default parameter) of non-empty: fragments to each frame of reference.
5. An optimal number of clusters is determined based on the following criteria:
   a. The minimum number of groups that yields a complete set of proteins in the combined lists from (4)
   b. LGA_S between any pair of proteins from the group is at least 60% (default cutoff), minimum value from (3.a). NOTE: In step (5.a) a minimum number of clusters is defined based on local similarities in non-empty fragments along the protein sequence using initially selected representative frames of reference. Step (5.b) allows reassignment of less similar structures from one cluster to another. It also allows subdivision of clusters in order to satisfy the requirements that within each cluster any pair of proteins has at least 60% overall structure similarity. This way less similar structures are not grouped together even if they satisfy the requirement regarding a common set of non-empty fragments (4).
6. For every cluster we select a representative as the structure that has the highest values determined in steps 3.a, b, and c. in comparison with other members of the cluster.

In summary, the STRALCP Engine 200 provides the following features:
   pair-wise comparison of hundreds of protein structures to a single protein structure.
   identification of pair-wise fragments and spans that are conserved within a set of protein structures.
   calculation of the minimum number of clusters required for a given set of protein structures.
   identification of a representative structure for each cluster
   definition of a "structural fingerprint "for each cluster defined by the representative structure and the set of spans that are shared by the protein structures in the cluster.
   ability to compare a new solved protein structure with the representative protein structure to determine whether the newly-solved structure should be included to the particular cluster, as opposed to re-clustering proteins based on newly-solved structures.

Reference in the specification to "one embodiment" or to "an embodiment" means that a particular feature, structure, or characteristic described in connection with the embodiments are included in at least one embodiment of the invention. The appearances of the phrase "in one embodiment" in various places in the specification are not necessarily all referring to the same embodiment.

Some portions of the above are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps (instructions) leading to a desired result. The steps are those requiring physical manipulations of physical quantities. Usually, though not necessarily, these quantities take the form of electrical, magnetic or optical signals capable of being stored, transferred, combined, compared and otherwise manipulated. It is convenient at times, principally for reasons of common usage, to refer to these signals as bits, values, elements, symbols, characters, terms, numbers, or the like. Furthermore, it is also convenient at times, to refer to certain arrangements of steps requiring physical manipulations of physical quantities as modules or code devices, without loss of generality.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or "determining" or the like, refer to the action and processes of a computer system, or similar electronic computing device, that manipulates and transforms data represented as physical (electronic) quantities within the computer system memories or registers or other such information storage, transmission or display devices.

Certain aspects of the present invention include process steps and instructions described herein in the form of an algorithm. It should be noted that the process steps and instructions of the present invention can be embodied in software, firmware or hardware, and when embodied in software, can be downloaded to reside on and be operated from different platforms used by a variety of operating systems.

The present invention also relates to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The algorithms and displays presented herein are not inherently related to any particular computer or other apparatus. Various general-purpose systems may also be used with programs in accordance with the teachings herein, or it may prove convenient to construct more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein, and any references below to specific languages are provided for disclosure of enablement and best mode of the present invention.

While the invention has been particularly shown and described with reference to a preferred embodiment and several alternate embodiments, it will be understood by persons skilled in the relevant art that various changes in form and details can be made therein without departing from the spirit and scope of the invention.

Finally, it should be noted that the language used in the specification has been principally selected for readability and instructional purposes, and may not have been selected to delineate or circumscribe the inventive subject matter. Accordingly, the disclosure of the present invention is intended to be illustrative, but not limiting, of the scope of the invention, which is set forth in the following claims.

Protein Structure Modeling

Advances in protein structure prediction or modeling provide methods of computationally solving the set of atom coordinates for a given protein. According to the embodiment of the present invention, it may be necessary to generate a computationally solved or 'modeled' protein structure for one or more proteins identified for clustering, where the protein does not have an experimentally-solved protein structure. The Sequence to Structure Module 210 functions to generate computationally solved protein structures based on three different techniques (sequence comparison—homology modeling, threading and ab initio modeling). The Sequence to Structure Module 210 typically generates computationally solved protein structure prediction using a combination of these techniques.

A favored method in the art of protein structure prediction is to find a close homolog for which the structure is known. CASP (Critical Assessment of Techniques for Protein Structure Prediction) (Moult et al., 2003) experiments have shown that protein structure prediction methods based on homology search techniques are still the most reliable prediction methods. Sequence comparison and threading techniques are based on homology search.

Sequence comparison approaches to protein structure prediction are popular due to availability of protein sequence information. These techniques use conventional sequence search and alignment techniques such as BLAST or FASTA to assign protein fold to the query sequence based on sequence similarity.

Approaches which use protein profiles are similar to sequence-sequence comparisons. A protein profile is an n-by-20 substitution matrix where n is the number of residues for a given protein. The substitution matrix is calculated via a multiple sequence alignment of close homologs of the protein. These profiles may be searched directly against sequence or compared with each other using search and alignment techniques such as PSI-BLAST and HMMER.

It is known that sequence similarity is not necessary for structural similarity. Proteins sharing similar structure can have negligible sequence similarity. Convergent evolution can drive completely unrelated proteins to adopt the same fold. Accordingly, 'threading' methods of protein structure prediction were developed which use sequence to structure alignments. In threading methods, the structural environment around a residue could be translated into substitution preferences by summing the contact preferences of surrounding amino acids. Knowing the structure of a template, the contact preferences for the 20 amino acids in each position can be calculated and expressed in the form of an n-by-20 matrix. This profile has the same format as the position specific scoring profile used by sequence alignment methods, such as PSI-BLAST, and can be used to evaluate the fitness of a sequence to a structure.

Ab initio methods are aimed at finding the native structure of the protein by simulating the biological process of protein folding. These methods perform iterative conformational changes and estimate the corresponding changes in energy. Ab initio methods are complicated by inaccurate energy functions and the vast number of possible conformations a protein chain can adopt. The most successful approaches of ab initio modeling include lattice-based simulations of simplified protein models and methods building structures from fragments of proteins. Ab initio methods demand substantial computational resources and are also quite difficult to use, and expert knowledge is needed to translate the results into biologically meaningful results. Despite known limitations, Ab initio methods are increasingly applied in large-scale annotation projects, including fold assignments for small genomes. Recent examples of such applications include Bonneau et al. 2001, Kuhlman et al. 2003 and Dantas et al. 2003.

In practice, protein structure prediction typically involves a combination of the listed techniques, both experimental and computational. Hybrid approaches to protein structure prediction involve using different techniques for solving the atom coordinates at different stages or to solve for different parts of the protein structure. An example of this would be the use of AS2TS (amino acid to tertiary structure, a homology based modeling technique) to facilitate the molecular replacement (MR) phasing technique in experimental X-ray crystallographic determination of the protein structure of *Mycobacterium tuberculosis* (MTB) RmlC epimerase (Rv3465) from the strain H37rv. The AS2TS system was used to generate two homology models of this protein that were then successfully employed as MR targets.

Meta-predictors or consensus approaches attempt to benefit from the diversity of models by combining multiple techniques. In these methods, predictive models are collected and analyzed from a variety of different computational and experimental techniques. A common approach for combining models by consensus is to select the most abundant fold represented in the set of high scoring models. Other approaches to consensus modeling involve structural clustering such as HCPM-Hierarchical Clustering of Protein Models (Gront and Kolinski, 2005).

REFERENCES

Redfern, O., Grant, A., Maibaum, M., Orengo, C. (2005) Survey of current protein family databases and their application in comparative, structural and functional genomics. Journal Of Chromatography B-Analytical Technologies In The Biomedical And Life Sciences, 815 (1-2), 97-107.

Berman, H. M., Westbrook, J., Feng, Z., Gilliland, G., Bhat, T. N., Weissig, H., Shindyalov, I. N., and Bourne, P. E. (2000) The protein data bank. Nucleic Acids Research, 8, 235-242.

Murzin, A. G., Brenner, S. E., Hubbard, T., Chothia, C. (1995) SCOP: a structural classification of proteins database for the investigation of sequences and structures. J. Mol. Biol., 247, 536-540.

Orengo, C. A., Michie, A. D., Jones, S., Jones, D. T., Swindells, M. B., and Thornton, J. M. (1997) CATH—A Hierarchic Classification of Protein Domain Structures. Structure. Vol 5, No 8, 1093-1108.

Altschul, S. F., Madden, T. L., Scaffer, A. A., Zhang, J., Zhang, Z., Miller, W., Lipman, D. J. (1997) Gapped BLAST and PSI-BLAST: a new generation of protein database search programs. Nucleic Acids Research, 25, 3389-3402.

Ortiz, A. R., Strauss, C. E., Olmea, O. (2002) MAMMOTH (matching molecular models obtained from theory): an automated method for model comparison. Protein Sci, 11, 2606-2621.

Huan, J., Wang, W., Washington, A., Prins, J., Shah, R., and Tropsha, A. (2004) Accurate classification of protein structural families using coherent subgraph analysis. Pac. Symp. Biocomput. 411-422.

Zemla, A. (2003) LGA—A Method for Finding 3D Similarities in Protein Structures. Nucleic Acids Research, Vol. 31, No. 13, 3370-3374.

Geisbrecht, B. V., Hamaoka, B. Y., Perman, B., Zemla, A., Leahy, D. J. (2005) The crystal structures of EAP domains from *Staphylococcus aureus* reveal an unexpected homology to bacterial superantigens. Journal Of Biological Chemistry, 280 (17), 17243-17250.

Zemla, A., Ecale Zhou, C., Slezak, T., Kuczmarski, T., Rama, D. Torres, C., Sawicka, D., Barsky, D. (2005) AS2TS System for Protein Structure Modeling and Analysis. Nucleic Acids Research, 33, W111-W115.

Moult, J., Fidelis, K., Zemla, A. (2003) Hubbard T., Critical assessment of methods of protein structure prediction (CASP)-round V., Proteins.; 53 Suppl 6:334-9.

Dantas, G., Kuhlman, B., Callender, D., Wong, M. and Baker, D. (2003) A large scale test of computational protein design: folding and stability of nine completely redesigned globular proteins. J. Mol. Biol., 332, 449-460.

Hakansson, M., Petersson, K., Nilsson, H., Forsberg, G., Bjork, P., Antonsson, P., Svensson, L. A. (2000) The crystal structure of staphylococcal enterotoxin H: implications for binding properties to MHC class II and TcR molecules. J. Mol. Biol., 302, 527-537.

Al-Shangiti, A., Naylor, C., Nair, S., Briggs, D., Henderson, B., Chain, B. (2004) Structural Relationships and Cellular Tropism of Staphylococcal Superantigen-Like. Proteins Infect. Immun., 72, 4261-4270.

Arcus, V. L., Langley, R., Proft, T., Fraser, J. D., Baker, E. N. (2002) The three-dimensional structure of a superantigen-like protein, SET3, from a pathogenicity island of the *Staphylococcus aureus* genome. J. Biol. Chem., 277, 32274-32281.

Earhart, C. A., Mitchell, D. T., Murray, D. L., Pinheiro, D. M., Matsumura, M., Schlievert, P. M., Ohlendorf, D. H. (1998) Structures of five mutants of toxic shock syndrome toxin-1 with reduced biological activity. Biochemistry, 37, 7194-7202.

Prasad, G. S., Radhakrishnan, R., Mitchell, D. T., Earhart, C. A., Dinges, M. M., Cook, W. J., Schlievert, P. M., Ohlendorf, D. H. (1997) Refined structures of three crystal forms of toxic shock syndrome toxin-1 and of a tetramutant with reduced activity. Protein Sci., 6, 1220-1227.

Bonneau, R., Tsai, J., Ruczinski, I. and Baker, D. (2001) Functional inferences from blind ab initio protein structure predictions. J. Struct. Biol., 134, 186-190.

Kuhlman, B., Dantas, G., Ireton, G. C., Varani, G., Stoddard, B. L. and Baker, D. (2003) Design of a novel globular protein fold with atomic-level accuracy. Science, 302, 1364-1368. 61.

Bower, M. J., Cohen, F. E. and Dunbrack, R. L. (1997) Prediction of protein side-chain rotamers from a backbone-dependent rotamer library: a new homology modeling tool. J Mol Biol, 267, 1268-1282.

Canutescu A. A., Shelenkov A. A. and Dunbrack, R. L. (2003) A graph theory algorithm for protein side-chain prediction. Prot Sci, 12 ,2001-2014.

Gront D., Kolinski A., HCPM—program for hierarchical clustering of protein models. Bioinformatics. July 15;21 (14):3179-80. Epub 2005 Apr. 19.

What is claimed is:

1. A computer-implemented method for clustering a set of three dimensional protein structures, the method comprising:
identifying, by a computer, the set of three dimensional protein structures, each three-dimensional protein structure comprising a polypeptide sequence and structural coordinates;
generating, by the computer, a structural alignment of the set of three-dimensional protein structures;
for each pair of protein structures in the aligned set:
designating, by the computer, a first protein structure of the pair as a reference protein structure;
generating, by the computer, a first plurality of fragments for the reference protein structure, each fragment comprising a polypeptide subsequence of contiguous residues of a pre-determined length and associated distances of structural coordinates of contiguous residue pairs;
generating, by the computer, a second plurality of fragments for a second protein structure in the pair, each fragment comprising a polypeptide subsequence of contiguous residues of the pre-determined length and associated distances of structural coordinates of contiguous residue pairs;
performing, by the computer, a local structural comparison of the distances of structural coordinates of contiguous residue pairs between the first plurality of fragments and the second plurality of fragments using a first distance cutoff value;
identifying, by the computer, candidate spans consisting of a plurality of contiguous residue pairs from the first plurality of fragments and the second plurality of fragments having structural coordinates within the first distance cutoff value;
determining, by the computer, a pair-wise local similarity value that indicates the number of fragments from the first plurality of fragments and from the second plurality of fragments that share candidate spans;
assigning, by the computer, the identified candidate spans and the pair-wise local similarity value to the reference protein structure;
generating, by the computer, a matrix of identified candidate spans for each of the pairs of protein structures; and
generating, by the computer, a first cluster of protein structures based on the matrix of identified candidate spans, each cluster having protein structures with at least a pre-determined number of fragments that share candidate spans, thereby clustering the set of three-dimensional protein structures.

2. The method of claim 1, wherein the first distance cutoff value is a root mean square deviation of 0.5 Angstroms.

3. The method of claim 1, wherein the candidate span has a minimum number of residue pairs.

4. The method of claim 3, wherein the minimum number of residue pairs is 3 residue pairs.

5. The method of claim 1, wherein at least 80% of the fragments of the protein structures in each cluster share candidate spans.

6. The method of claim 1, further comprising:
for each pair of protein structures in a cluster:
performing a global structural comparison of the distances of structural coordinates of contiguous residue pairs in a first protein structure of the pair and a second protein structure of the pair using a second distance cutoff value;
determining a pair-wise global similarity value for the global structural similarity between the first protein structure and a second protein structure; and
generating a second set of clusters of protein structures from the first set of clusters of protein structures based on the pair-wise global similarity values.

7. The method of claim 6, wherein the pair-wise global homology value indicates that at least 60% of the residues in the first protein structure and second protein structure form a plurality of residue pairs, wherein a structural coordinate of each member of each residue pair falls within the second distance cutoff value.

8. The method of claim 7, wherein the second distance cutoff value is 5.0 Angstroms.

9. The method of claim 6, wherein the pair-wise global homology value is a local-global alignment (LGA_S) score.

10. The method of claim 6, further comprising:
selecting by the computer a representative protein structure for each cluster in the second set of cluster of protein structures, based on the pair-wise local similarity values and the pair-wise global similarity values.

11. The method of claim 1 wherein a protein structure of the set of protein structures is an experimentally determined protein structure.

12. A non-transitory computer-readable storage medium storing executable computer program instructions for clustering a set of three dimensional protein structures, the computer program instructions comprising instructions for:
identifying, by a computer, the set of three dimensional protein structures, each three dimensional protein structure comprising a polypeptide sequence and structural coordinates;
generating, by the computer, a structural alignment of the set of three dimensional protein structures;
for each pair of protein structures in the aligned set:
designating, by the computer, a first protein structure of the pair as a reference protein structure;
generating, by the computer, a first plurality of fragments for the reference protein structure, each fragment comprising a polypeptide subsequence of contiguous residues of a pre-determined length and associated distances of structural coordinates of contiguous residue pairs;
generating, by the computer, a second plurality of fragments for a second protein structure in the pair, each fragment comprising a polypeptide subsequence of contiguous residues of the pre-determined length and associated distances of structural coordinates of contiguous residue pairs;
performing, by the computer, a local structural comparison of the distances of structural coordinates of contiguous residue pairs between the first plurality of fragments and the second plurality of fragments using a first distance cutoff value;
identifying, by the computer, candidate spans consisting of a plurality of contiguous residue pairs from the first plurality of fragments and the second plurality of fragments having structural coordinates within the first distance cutoff value;
determining, by the computer, a pair-wise local similarity value that indicates the number of fragments from the first plurality of fragments and from the second plurality of fragments that share candidate spans;
assigning, by the computer, the identified candidate spans and the pair-wise local similarity value to the reference protein structure;
generating, by the computer, a matrix of identified candidate spans for each of the pairs of protein structures; and
generating, by the computer, a first cluster of protein structures based on the matrix of identified candidate spans, each cluster having protein structures with at least a pre-determined number of fragments that share candidate spans, thereby clustering the set of three-dimensional protein structures.

13. The computer-readable non-transitory storage medium of claim 12, wherein the first distance cutoff value is RMSD=0.5 Angstroms.

14. The computer-readable non-transitory storage medium of claim 12, wherein the candidate span includes a minimum number of residue pairs.

15. The computer-readable non-transitory storage medium of claim 14, wherein the minimum number of residue pairs is 3 residue pairs.

16. The computer-readable non-transitory storage medium of claim 12, wherein at least 80% of the fragments of the protein structures in each cluster share candidate spans.

17. The computer-readable non-transitory storage medium of claim 12, further comprising:
for each pair of protein structures in a cluster:
performing a global structural comparison of the distances of structural coordinates of contiguous residue pairs in a first protein structure of the pair and a second protein structure of the pair using a second distance cutoff value;
determining a pair-wise global similarity value for the global similarity between the first protein structure and a second protein structure; and
generating a second set of clusters of protein structures from the first set of clusters of protein structures based on the pair-wise global similarity values.

18. The computer-readable non-transitory storage medium of claim 17, wherein the pair-wise global homology value indicates that at least 60% of the residues in the first protein structure and second protein structure form a plurality of residue pairs, wherein a structural coordinate of each member of each residue pair falls within the second distance cutoff value.

19. The computer-readable non-transitory storage medium of claim 18, wherein the second cutoff distance is 5.0 Angstroms.

20. The computer-readable non-transitory storage medium of claim 17, wherein the pair-wise global homology value is a local-global alignment (LGA_S) score.

21. The method of claim 1, wherein a protein structure of the set of protein structures is a computationally modeled protein structure.

* * * * *